United States Patent
Russell et al.

(10) Patent No.: US 7,120,483 B2
(45) Date of Patent: Oct. 10, 2006

(54) METHODS FOR ANALYTE SENSING AND MEASUREMENT

(75) Inventors: Geoffrey A. Russell, Beaverton, OR (US); W. Kenneth Ward, Portland, OR (US); Ellen M. Anderson, Tualatin, OR (US); Jonathan D. Birck, Portland, OR (US)

(73) Assignee: iSense Corporation, Portland, OR (US)

( * ) Notice: Subject to any disclaimer, the term of this patent is extended or adjusted under 35 U.S.C. 154(b) by 14 days.

(21) Appl. No.: 10/694,264

(22) Filed: Oct. 27, 2003

(65) Prior Publication Data

US 2004/0138543 A1 Jul. 15, 2004

Related U.S. Application Data

(63) Continuation-in-part of application No. 10/342,144, filed on Jan. 13, 2003.

(51) Int. Cl.
*A61B 5/05* (2006.01)
*A61B 5/00* (2006.01)

(52) U.S. Cl. .................. 600/345; 600/347; 600/365

(58) Field of Classification Search ............. 600/309, 600/322–333, 339, 341, 345, 347–361, 364, 600/365; 204/403.01–403.14
See application file for complete search history.

(56) References Cited

U.S. PATENT DOCUMENTS

| | | | | |
|---|---|---|---|---|
| 4,671,288 A | * | 6/1987 | Gough | 600/347 |
| 4,711,245 A | * | 12/1987 | Higgins et al. | 204/403.1 |
| 4,953,552 A | * | 9/1990 | DeMarzo | 600/347 |
| 5,181,995 A | * | 1/1993 | Kummer | 205/464 |
| 5,510,266 A | | 4/1996 | Bonner et al. | 436/43 |
| 5,820,622 A | * | 10/1998 | Gross et al. | 604/890.1 |
| 5,871,494 A | | 2/1999 | Simons et al. | 606/181 |
| 6,083,710 A | * | 7/2000 | Heller et al. | 600/347 |
| 6,193,873 B1 | * | 2/2001 | Ohara et al. | 205/792 |
| 6,352,514 B1 | | 3/2002 | Douglas et al. | 600/583 |
| 6,561,989 B1 | * | 5/2003 | Whitson | 600/573 |
| 6,706,159 B1 | | 3/2004 | Moerman et al. | 204/403.03 |
| 6,793,632 B1 | * | 9/2004 | Sohrab | 600/573 |
| 2003/0217918 A1 | | 11/2003 | Davies et al. | 204/403.14 |
| 2003/0223906 A1 | * | 12/2003 | McAllister et al. | 422/58 |

* cited by examiner

*Primary Examiner*—Robert L. Nasser
*Assistant Examiner*—Patricia Mallari
(74) *Attorney, Agent, or Firm*—Schwabe Williamson & Wyatt

(57) ABSTRACT

A method of measuring an analyte concentration in body fluid. The method includes the use of an analyte measuring device that has an analyte sensing element with a sharpened distal end and further has an indicating electrode covered by an absorbent layer. Also, an electric power, data processing and display device is adapted to mate to and activate the analyte sensing element by applying electric power to it and adapted to receive the raw analyte measurement and to compute and display a refined analyte measurement from the raw analyte measurement. The analyte sensing element is introduced into the animal body, thereby placing the absorbent layer into contact with the body fluid. The absorbent layer becomes saturated with body fluid and the analyte sensing element is removed from the body and is activated to form a raw analyte measurement. Which is used to form and display a refined analyte measurement.

19 Claims, 4 Drawing Sheets

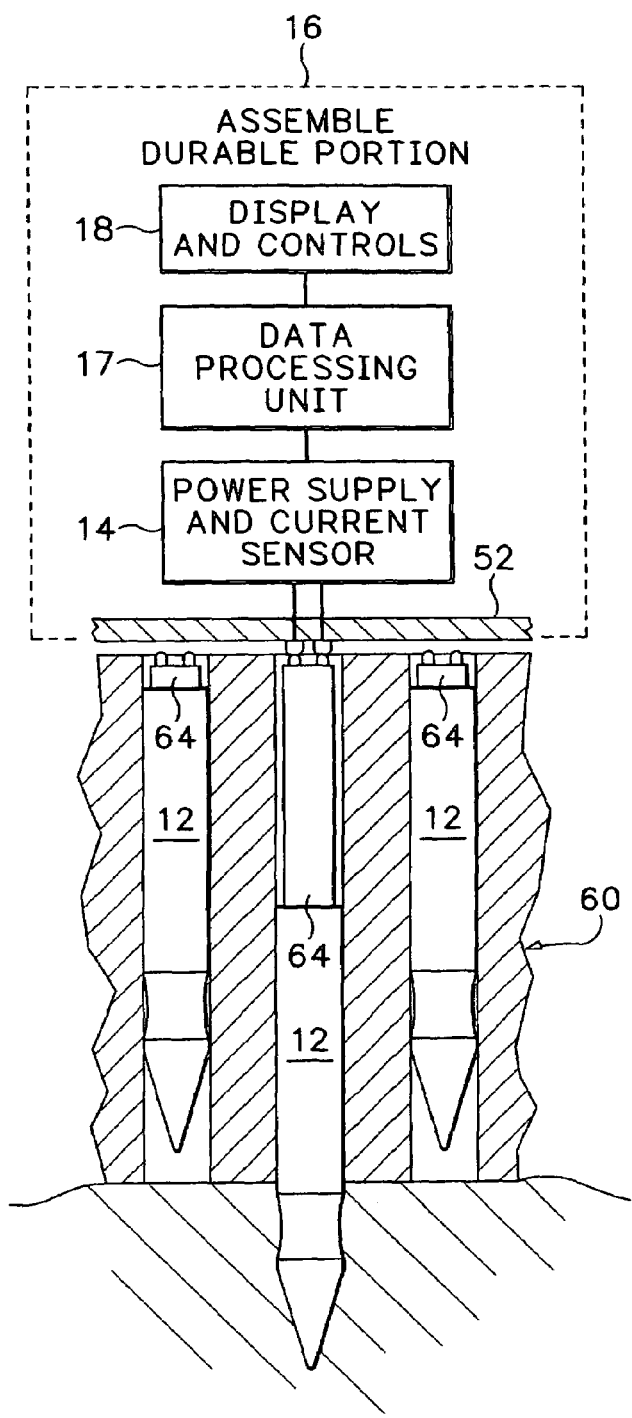
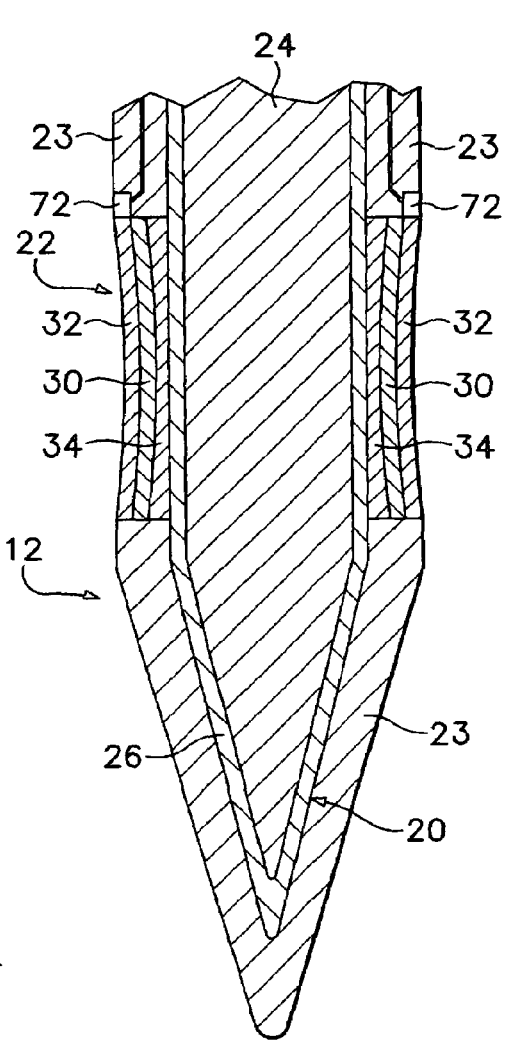
FIG.1
FIG.2

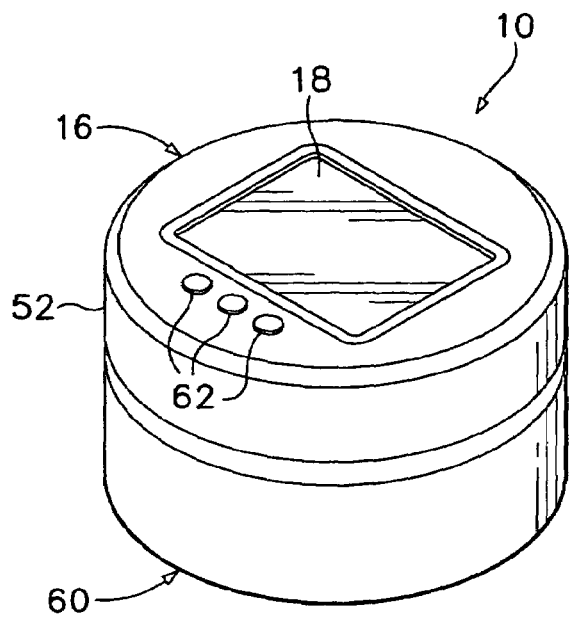
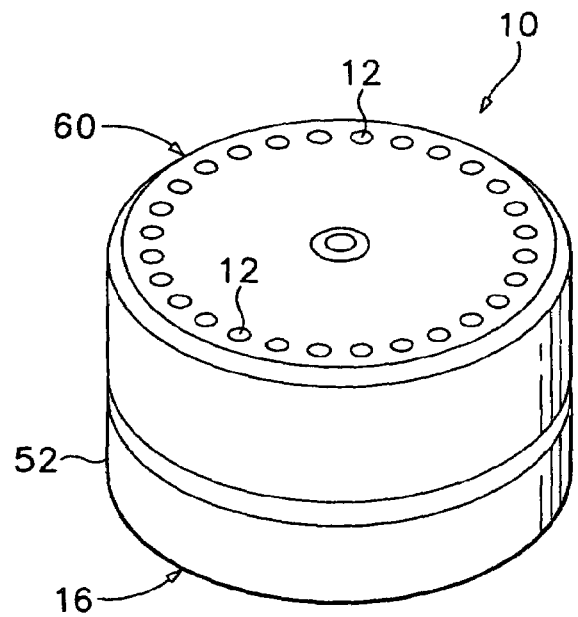
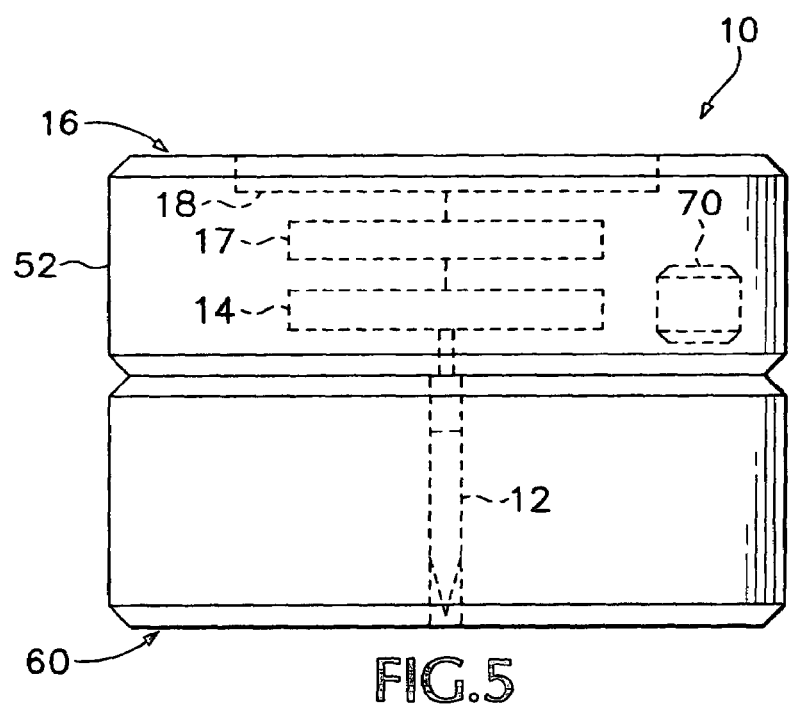

METHODS FOR ANALYTE SENSING AND MEASUREMENT

RELATED APPLICATIONS

This application is a continuation-in-part of application Ser. No. 10/342,144 filed Jan. 13, 2003.

BACKGROUND OF THE INVENTION

Among the other unpleasant aspects of having the disorder diabetes mellitus is the need to frequently test one's blood glucose concentration. With current technology a diabetic patient must prick his own fingertip or other body part with a lancet in order to withdraw blood from the wound. The fingertip is preferred because of the great number of capillaries located there.

The breach created through the skin by the lancet must be wide enough to permit blood to flow through. Human epidermis around the fingertips is on the order of 1–3 millimeters thick. Also, similar to other flexible, sheet like materials, skin tends to close up on itself if breached. Accordingly the lancet used must create a breach that is wide enough to not be closed by the natural action of the skin.

Moreover, the task of sampling one's own blood has generally required that a flat surface be present for the patient to arrange various test articles including a test strip, a lancet and a cotton ball with alcohol, for sterilizing the wound. As a result, it has heretofore been impossible for a diabetic patient to measure his blood glucose level in a public place without drawing attention to himself. Interviews with diabetic patients indicate that the workplace, where there is frequently a definite lack of privacy and where maintaining the secrecy of personal information may be greatly desired, presents particular difficulties.

A number of disclosures are aimed at easing this requirement by providing an integrated unit having a number of lancets and associated test articles (such as a test strip or a sensing cavity to be filled with blood drawn out from the body) and in which both lancet and test article are contemporaneously moved into test position. These devices tend to use chemical test strips, rendering them rather bulky and typically requiring the user to place a test strip in place before use.

In addition, a number of disclosures are directed at an implantable or insertable sensor, for continuous glucose monitoring. Although this technology appears to bear promise it is desirable to have additional options for the diabetic patient. For example, a method of quickly and easily making an occasional determination of blood glucose concentration would be helpful for patients not wishing to wear a glucose monitor.

Ease of use is not only an important consideration from the perspective of patient comfort, but also from the perspective of patient health. The easier it is for a patient to take his blood glucose level reading, the more frequently he is likely to do so. In turn, with more frequent measurements, the patient is likely to do a better job at regulating his glucose level and thereby avoiding chronic complications in which body tissue is damaged by toxic glucose levels or acute complications in which the patient is in danger of entering a state of hypoglycemic shock. Moreover, by more frequently measuring his or her glucose levels, the patient will likely form a better understanding of his body's response to the consumption of varying types of food and of varying degrees of physical exertion. The better the patient understands his body's response characteristics the better he will be able to tailor his eating, exercise and insulin injection or ingestion regime.

SUMMARY

In a first separate aspect, the present invention is a method of measuring an analyte concentration in body fluid. The method includes the use of an analyte measuring device that has an analyte sensing element with a sharpened distal end and further has an indicating electrode covered by an absorbent layer. Also, an electric power, data processing and display device is adapted to mate to and activate the analyte sensing element by applying electric power to it and adapted to receive the raw analyte measurement and to compute and display a refined analyte measurement from the raw analyte measurement. The analyte sensing element is introduced into the body of the subject, thereby placing the absorbent layer into contact with the body fluid. The absorbent layer becomes saturated with body fluid and the analyte sensing element is removed from the body and is activated to perform a raw analyte measurement which is used to calculate and display a refined analyte measurement.

In a second separate aspect, the present invention is an analyte sensing element adapted to be introduced into the body and removed from the body in a time period of less than about 2 seconds. The sensing element includes a rigid longitudinal body having a sharpened distal end to facilitate introduction into the body and an indicating electrode covered by an absorbent layer located on the rigid longitudinal body.

In a third separate aspect the present invention is a set of analyte sensing elements, each of which includes a rigid longitudinal body having a sharpened distal end to facilitate introduction into the body. In addition, each sensing element has an indicating electrode covered by an absorbent layer located on the rigid longitudinal body. All of the absorbent layers are adapted to absorb an equal amount of body fluids, to a tolerance of 10%.

In a fourth separate aspect, the present invention is an analyte measuring device that includes an analyte sensing element with a sharpened distal end to facilitate introduction into an animal body. The sensing element also has an indicating electrode covered by an absorbent layer. The device also includes an electric power, data processing and display assembly adapted to mate to the analyte sensing element and activate the analyte sensing element by applying electric power to it and adapted to receive the raw analyte measurement and to compute and display a refined analyte measurement, related to the raw analyte measurement.

In a fifth separate aspect, the present invention is an analyte sensing element, having an electrochemically active surface, sealingly covered by a layer that includes a conductive, redox mediating polymer. In one preferred embodiment, this polymer is in turn covered by an enzyme and enzyme cofactor layer. In an alternative preferred embodiment, the enzyme and enzyme cofactor are mixed into the layer that includes a conductive, redox mediating polymer.

In a sixth separate aspect the present invention is a method of making an analyte sensing element. First, a substrate having an electrochemically active surface is provided. Next, a sealing layer that includes a conductive, redox mediating polymer is formed onto said electrochemically active surface.

In a seventh separate aspect the present invention is an analyte sensing element comprising an electrochemically active surface and a layer comprised of a conductive, redox mediating polymer, sealingly applied to the electrochemically active surface. In addition, a layer that includes an enzyme and an enzyme cofactor mixed with absorbent material coats the conductive, redox mediating polymer.

The foregoing and other objectives, features and advantages of the invention will be more readily understood upon consideration of the following detailed description of the invention, taken in conjunction with the accompanying drawings.

BRIEF DESCRIPTION OF THE DRAWINGS

FIG. 1 is a partially schematic representation, partially cross-sectional view of a glucose sensing assembly according to the present invention.

FIG. 2 is an expanded cross-sectional view of a glucose-sensing element of the glucose sensing assembly of FIG. 1.

FIG. 3 is a top perspective of the glucose sensing assembly of FIG. 1.

FIG. 4 is a bottom perspective of the glucose sensing assembly of FIG. 1.

FIG. 5 is a side view of the glucose sensing assembly of FIG. 1.

DETAILED DESCRIPTION OF THE PREFERRED EMBODIMENT

Figure 6:
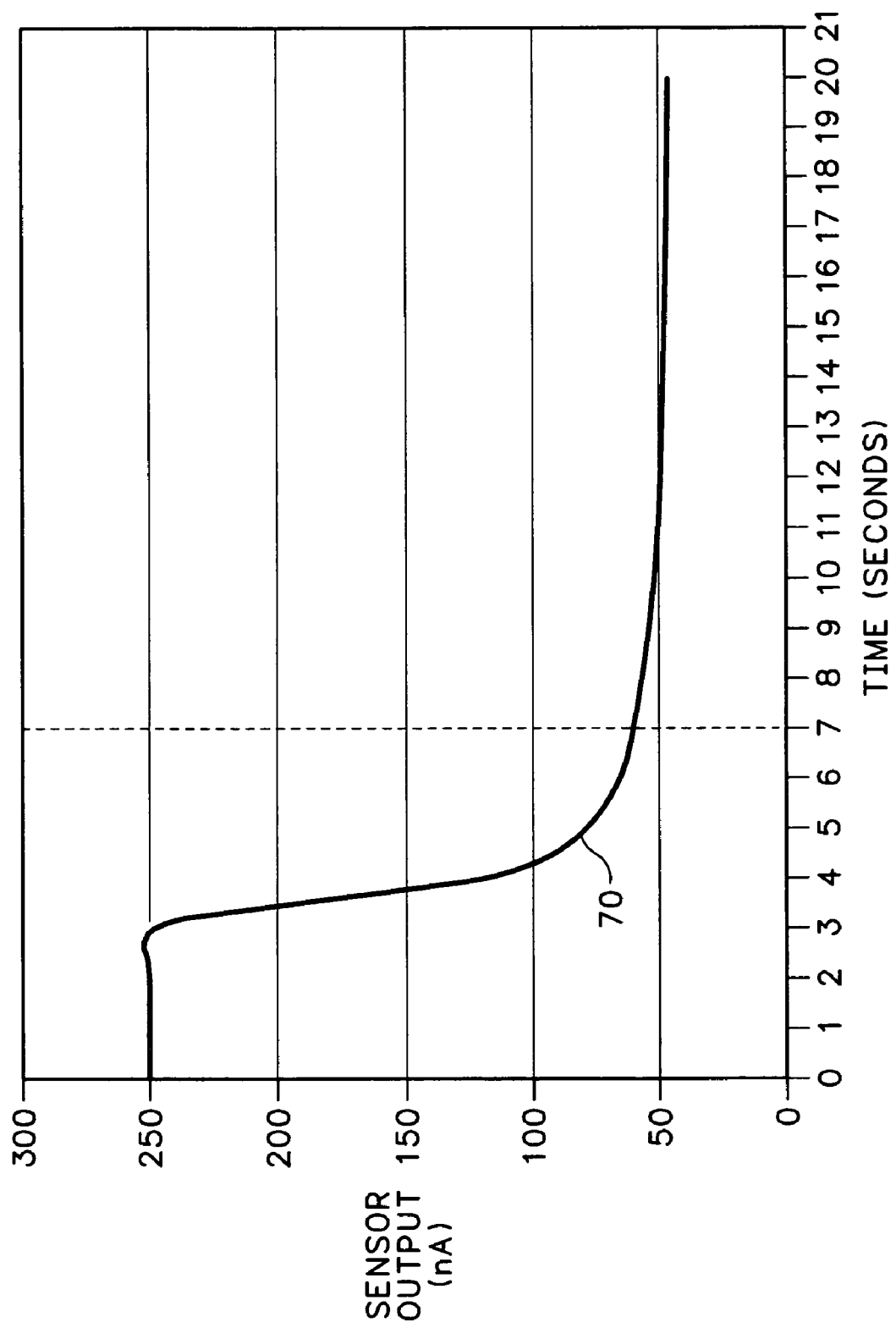
FIG. 6 is a set of graphs showing current versus time for a glucose-sensing element, such as that of FIG. 2, when introduced into any one of three different concentrations of glucose.

Referring to FIG. 1 a preferred embodiment of the present invention is a glucose sensor assembly 10 having a sensing element 12 that is adapted to be briefly introduced into the soft tissue of a patient. A power supply and current sensor unit 14, which is housed in an assembly durable portion 16, supplies the sensing element 12 with power. Sensing unit 14 quickly (<20 seconds) responds to introduction into the soft tissue of a patient by producing a sensing current that is generally proportional to the glucose level in this tissue. This current may be considered a "raw analyte measurement." A data processing unit 17, measures the magnitude of this current, computes a best estimate glucose concentration (or a "refined analyte measurement") and sends this information to a controls and display unit 18, which displays this estimate on a small liquid crystal display. Units 14, 17 and 18 may be collectively termed an "electric power, data processing and display device." It should be noted that although in one preferred embodiment, described above, a fixed voltage is provided and a current is measured, in an alternative preferred embodiment, a fixed current is provided and the voltage across sensing element 14 is measured and is accordingly, the "raw analyte measurement."

Because sensing element 12 yields the sensing current during its brief indwell period, there is no need to withdraw blood from the body. As a result, sensing element 12 is thinner at its distal end (<300 micrometers thick) than lancets adapted to create a puncture through the skin that is sufficient to permit blood flow therethrough.

Referring to FIG. 2, sensing element 12 includes a bimetallic needle 20 that in conjunction with a membrane system 22 reacts to the presence of glucose and oxygen to act as an indicating electrode. Needle 20 is coated with a protective layer 23, made of durable, non-toxic material such as polyimide, except for where coated by membrane system 22. In production, protective layer 23 is dip-coated onto needle 22 and then removed, preferably with an excimer or ND:YAG laser, in the area in which membrane system 22 is to be applied.

Needle 20 has a diameter of 227 microns and has a needle core 24 of structurally robust material such as stainless steel that is 226 microns thick and an electrochemically active plating 26, such as platinum, that is less than a micron thick. Alternative structurally robust materials that may be used for inner core 24 are tantalum, tungsten, stainless steel or nitinol. Although copper is forbidden in implants, as it is quite toxic, an inner core 24 of copper is possible in this application because needle 20 only briefly (typically <5 seconds) resides in the body.

In a preferred method of producing a thin platinum coating over stainless steel, a strike, or extremely thin (<1 nm) coating of gold is first electroplated onto the stainless steel core. Then, platinum is electroplated in a bath having a current density on the order of 40 amperes/ft$^2$ or less. It is important to electroplate with a comparatively low current density, causing a slow buildup of platinum, in order to prevent uneven growth of the platinum layer.

Although as noted, needle 20 may be a core 24 with plating 26, other embodiments are also possible. For example, needle 20 may be made from a drawn filled tube that has been cut and sharpened or cut on a bias, to make it sharp, or which is naturally sharp, as it is very thin. In another alternative, needle 20 includes a core of structurally robust material that is covered with an outer layer 26 that is made of foil of electrochemically active material such as platinum. In alternative preferred embodiments outer layer 26 may be palladium or gold.

The membrane system 22 must perform a number of functions. First, it must provide an enzyme that reacts with glucose and oxygen to form peroxide or some other electrochemically active species. A reactive layer 30 of glucose oxidase, glutaraldehyde and albumin produces hydrogen peroxide when contacted by glucose and oxygen, performs this function.

Second, because glucose is far more prevalent in the blood and other body fluids than oxygen, system 22 must include a membrane placed over the reactive layer 30 to permit a greater permeation of oxygen than glucose, so that the glucose concentration measurement is not limited by the oxygen concentration in the immediately surrounding tissue. This function is performed by a permselective hard block/soft block copolymer layer 32. This layer is of the type described in U.S. Pat. Nos. 5,428,123; 5,589,563 and 5,756,632, which are hereby incorporated by reference as if fully set forth herein. Layer 32 is preferably less than 10 microns thick, to permit rapid permeation by glucose and oxygen.

Third, membrane system 22 must prevent interferents, such as acetaminophen, from corrupting the measurement by causing current flow unrelated to the presence of glucose. This function is performed by an inner interferent reducing layer 34 of a compound such as sulfonated polyether sulfone, polyamino-phenol, or polypyrrole, in one embodiment 3-amino-phenol, which quickly permits the permeation of the hydrogen peroxide, which causes the current flow indicative of the concentration of glucose. Persons skilled in the relevant arts will readily recognize that quick permeation is highly desirable in a briefly indwelling sensor so that a measurement may be quickly obtained.

To produce sensing element 12, first the interferent reducing layer 34 of 3-amino-phenol is solution-coated or electro polymerized onto the surface of platinum plating 26. Layer 34 may be from a few nanometers to 2 microns thick, to permit rapid permeation by $H_2O_2$ ions, thereby reacting very quickly to glucose concentration. Over this the reactive layer 30 of glucose oxidase is dip-coated or electrodeposited. Glutaraldehyde is deposited on the glucose oxidase to immobilize the glucose oxidase. The sensor is dip coated in the soft block/hard block copolymer 32. In the finished product, the surface of the sensing region 22 is slightly depressed relative the remainder of the surface of sensing element 12. In one embodiment, the glucose oxidase 30 is applied before layer 34, which is electrodeposited through layer 30.

Figure 7:
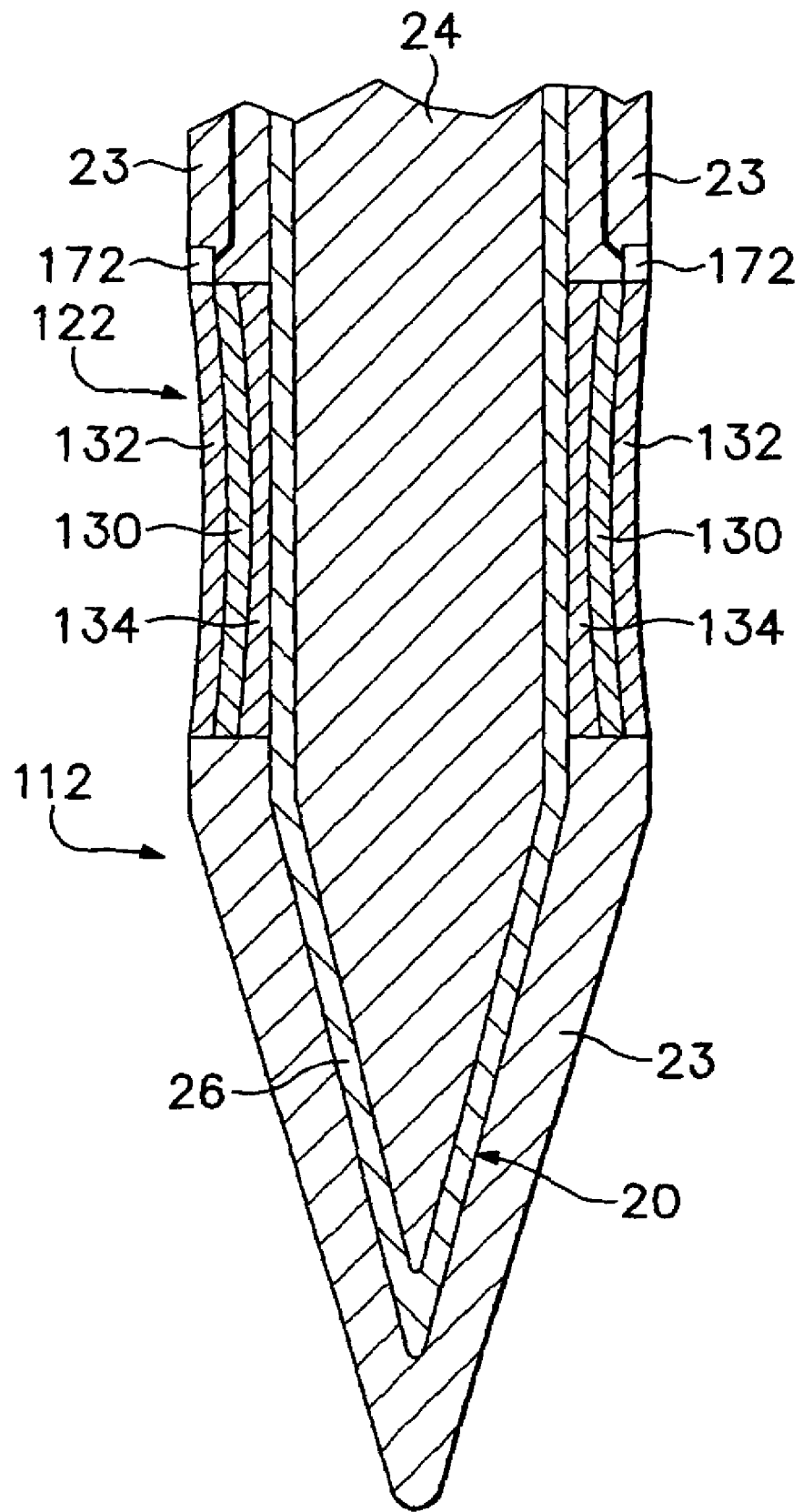
FIG. 7 is an expanded cross-sectional view of an alternative glucose sensing element adapted to form a part of the glucose sensing assembly of FIG. 1.

FIG. 7 illustrates an alternative embodiment of a sensing element 112, which may serve the same function as sensor 12 in the overall assembly 10. In FIG. 7, elements that are identical with the same element in FIG. 2 are given the same reference numbers and are not discussed anew. Homologous elements are given the same reference number plus 100. A membrane system 122 is structurally very different from system 22, and performs the function of detecting glucose in a very different manner, responding only to glucose concentration without respect to the presence of oxygen. A layer of redox mediator such as polyvinyl ferrocene, hydroquinone or dimethylferrocene 134 is polymerized or deposited directly onto the surface of platinum layer 26. This polymerization forms a close enough bond that interferents are unable to physically penetrate layer 134 to reach the platinum 26. As a consequence, layer 134 serves both as a redox mediator layer (thereby conductive) and as an interferent excluding layer. Middle layer 130 is a mixture of an enzyme and an enzyme cofactor. The enzyme may be either glucose dehydrogenase or glucose oxidase and the cofactor may be nicotinamide adenine dinucleotide (NAD), flavin adenine dinucleotide or a quinone-based enzyme cofactor. The cofactor shuttles electrons to layer 134, from whence they are shuttled to the platinum layer 26. In an alternative embodiement layers 134 and 130 are merged into a single layer (130, 134) of mixed enzyme, enzyme cofactor and redox mediator. This layer may be applied by electro polymerization in a bath having all three substances.

Layer 132 is a layer of absorbent material such as carboxymethylcellulose, gelatin, or a microporous coating composed of inorganic particles in a polymeric binder. This permits element 112 to be briefly introduced into human flesh and then withdrawn with the absorbent material 132 saturated with body fluids. Not only does this permit a brief period of sensor indwelling, but also assures a sample having a predetermined volume. Because spreading layer 132 assures a complete wetting of layer 130, elements 172 may serve as a reference electrode assembly.

For sensing assembly 10, in one embodiment, a case 52 of the durable portion 16 serves as a reference electrode. The user grasps the case 52 in his right hand (left hand if the patient is left handed) and pushes a sensing element 12 into either his left arm or a left hand fingertip. When sensing element 12 enters the user's flesh, the circuit is completed through the user's body. Other reference electrode structures can consist of the portion of the housing immediately surrounding the indicating electrode or a patch placed upon the skin.

Referring to FIGS. 3–5, sensing elements 12 are preferably disposable and are provided in a disposable magazine 60, which is releasably and matingly attached to durable portion 16. Magazine 60 is rotated either manually or by pressing one of a set of buttons 62 that are part of the controls and display unit 18. In the second option a small electric motor 70 is actuated that rotates magazine 60. In either embodiment, an unused sensing element is rotated to an activation position, where it is aligned with an opening through the bottom of case 52. When a sensing element 12 is rotated into place, it is automatically electrically connected to the power supply and current sensing unit 14. On command from one of the buttons 62, or in an alternative embodiment always upon arriving sensing element 12 arriving in place, a sensor physical actuation unit 64 pushes sensing element 12 outwardly so that it will enter the flesh of the patient if assembly 10 is correctly positioned against the patient's skin.

In one preferred embodiment the sensing element 12 is energized to a preset bias voltage level, which may be at a level of from 0.2 VDC to 0.8 VDC between cathode and anode, contemporaneously with being introduced into the patient. (We are currently examining whether there are advantages to using a lower bias voltage to eliminate some of the interferents.) In one embodiment a pair of contacts 72 positioned at the top of the sensing region 22 is electrically connected by body fluid when the sensing region 22 is entirely covered by body fluid. This is used to trigger the application of voltage to the sensing element 12.

After insertion the patient waits for approximately six seconds at which time the controls and display unit 18 provides a reading of the blood glucose level. After this, unit 64 pulls sensing element 12 back into magazine 60, where it is stored until all of magazine 60 is detached from the durable portion 16 and placed in a proper disposal receptacle. Subsequently, a new magazine 60 is attached into durable portion 16, for further measurements. To support this option, in a preferred method, new magazines 60, filled with sensors 12 are made and sold. Alternatively, the entire assembly 10 is disposable and comes as a single non-separable unit.

Referring to FIG. 6, which shows a graph 70 of early experimental readings (in current v. time coordinates) from a sensor according to the present invention after being placed in a solution of 5 mM glucose. The current reading at first entry into the solution is heavily corrupted by platinum oxidation and other, incompletely understood, factors. In one preferred embodiment the data processing unit 17, corrects the sensing element current by subtracting away a quantity representing the initial transient current at the moment the sensing element current is measured. To do this, a timing process is started at the moment when sensing element current is first detected. In one embodiment a set of corrected current measurements are averaged together to provide the reading. The correction for the anticipated initial transient current and the use of ultra-thin (for some embodiment less than 10 nanometers thick) membranes permits the calculation of a glucose concentration measurement within 20 seconds of the sensor being introduced into the patient's flesh. As noted, in a preferred embodiment a reading is provided in about 5 seconds. It is possible, in fact likely, that the glucose level will be changing as the unit is in the body.

Accordingly, in one preferred embodiment the direction of change, after correction for the initial transient current, is computed and displayed. In another embodiment a weighted average is formed of the corrected measurements, with more recent measurements being weighted more heavily, to give the patient a reading that reflects more heavily the more recent measurements. In yet another preferred embodiment, the processor simply waits until the initial transient current has dissipated, and then computes an instantaneous or brief period glucose concentration at the latest possible moment, in order to provide the patient with the timeliest information.

In an additional preferred embodiment, the signal processing unit 17 time tags and stores each glucose concentration estimate and uses this stream of time tagged estimates to send a value representing glucose concentration change to the controls and display unit 18.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

The invention claimed is:

1. A method of measuring an analyte concentration in body fluid in an animal body having skin and subcutaneous soft tissue that includes body fluid, said method comprising:
   (a) providing an analyte measuring device, including:
      (i) an analyte sensing element, having a sharpened distal end to facilitate introduction into said animal body and further having an indicating electrode covered by an absorbent or spreading layer forming an exterior surface of said analyte sensing element;
      (ii) an electric power, data processing and display device adapted to mate to said analyte sensing element and activate said analyte sensing element by applying electric power to it and adapted to receive said raw analyte measurement and to compute and display a refined analyte measurement, related to said raw analyte measurement;
   (b) introducing said analyte sensing element into said animal body subcutaneous soft tissue, thereby placing said absorbent layer into contact with said animal body subcutaneous soft tissue and said body fluid;
   (c) permitting said absorbent layer to become saturated with body fluid;
   (d) removing said indicating electrode from said body soft tissue;
   (e) activating said analyte sensing element after removing said indicating electrode from said body soft tissue by applying electric power to said analyte sensing element, thereby causing said analyte sensing element to form a raw analyte measurement; and
   (f) receiving said raw analyte measurement in said electric power, data processing and display device and computing and displaying a refined analyte measurement, related to said raw analyte measurement.

2. The method of claim 1 wherein an enzyme layer is interposed between said indicating electrode and said absorbent layer.

3. The method of claim 1 wherein a redox mediator layer is interposed between an enzyme layer and said indicating electrode.

4. The method of claim 1 wherein a permselective layer is interposed between an enzyme layer and said absorbent layer.

5. The method of claim 1 wherein an interferent excluding layer is interposed between an enzyme layer and said absorbent layer.

6. The method of claim 1, wherein, in step (d), said analyte sensing element is removed from said animal body within about 20 seconds of being introduced into said animal body.

7. The method of claim 1, wherein, in step (d), said analyte sensing element is removed from said animal body within about 5 seconds of being introduced into said animal body.

8. The method of claim 1 wherein an interferent excluding layer is interposed between an enzyme layer and said indicating electrode.

9. The method of claim 1 wherein said absorbent layer comprises carboxymethylcellulose.

10. The method of claim 1 wherein said absorbent layer comprises gelatin.

11. The method of claim 1 wherein said absorbent layer comprises a microporous coating comprising inorganic particles in a polymeric binder.

12. A method of measuring an analyte concentration in body fluid in an animal body, said method comprising:
    providing an analyte sensing element having an indicating electrode covered by an absorbent layer forming an exterior surface of said analyte sensing element;
    introducing said analyte sensing element into soft tissue of said animal body, thereby placing said absorbent layer into contact with said animal body soft tissue and said body fluid;
    removing said analyte sensing element from said animal body and then activating said analyte sensing element, thereby causing said analyte sensing element to form an analyte measurement; and
    receiving said analyte measurement.

13. The method of claim 12, further comprising permitting said absorbent layer to become saturated with body fluids prior to removing said analyte sensing element from said animal body.

14. The method of claim 12, further comprising removing said analyte sensing element from said animal body within about 20 seconds of being introduced into said animal body.

15. The method of claim 12, further comprising removing said analyte sensing element from said animal body within about 5 seconds of being introduced into said animal body.

16. The method of claim 12 wherein an interferent excluding layer is interposed between an enzyme layer and said indicating electrode.

17. The method of claim 12 wherein said absorbent layer comprises carboxymethylcellulose.

18. The method of claim 12 wherein said absorbent layer comprises gelatin.

19. The method of claim 12 wherein said absorbent layer comprises a microporous coating comprising inorganic particles in a polymeric binder.

\* \* \* \* \*